(12) United States Patent
Colvin et al.

(10) Patent No.: US 6,602,289 B1
(45) Date of Patent: Aug. 5, 2003

(54) ANNULOPLASTY RINGS OF PARTICULAR USE IN SURGERY FOR THE MITRAL VALVE

(75) Inventors: Stephen Colvin, New York, NY (US); Eugene Grossi, New York, NY (US); Aubrey Galloway, Bronxville, NY (US)

(73) Assignee: S&A Rings, LLC, New York, NY (US)

( * ) Notice: Subject to any disclaimer, the term of this patent is extended or adjusted under 35 U.S.C. 154(b) by 0 days.

(21) Appl. No.: 09/327,823

(22) Filed: Jun. 8, 1999

(51) Int. Cl.[7] ................................................. A61F 2/24
(52) U.S. Cl. ....................................................... 623/2.37
(58) Field of Search ................................. 623/2.36, 2.37, 623/2.38, 2.4, 2.41

(56) References Cited

U.S. PATENT DOCUMENTS

| | | | |
|---|---|---|---|
| 3,534,411 A | | 10/1970 | Shiley |
| 3,656,185 A | * | 4/1972 | Carpentier ................. 623/2.36 |
| 4,042,979 A | | 8/1977 | Angell |
| 4,164,046 A | * | 8/1979 | Cooley ....................... 623/2.36 |
| 4,204,283 A | | 5/1980 | Bellhouse et al. |
| 4,259,753 A | | 4/1981 | Liotta et al. |
| 4,364,126 A | | 12/1982 | Bosen et al. |
| 4,489,446 A | | 12/1984 | Reed |
| 4,655,773 A | | 4/1987 | Grassi |
| 4,917,698 A | * | 4/1990 | Carpentier et al. ........ 623/2.36 |
| 5,064,431 A | | 11/1991 | Gilbertson et al. |
| 5,104,407 A | * | 4/1992 | Lam et al. ................. 623/2.36 |
| 5,163,953 A | | 11/1992 | Vince |
| 5,326,372 A | | 7/1994 | Mhatre et al. |
| 5,350,420 A | | 9/1994 | Cosgrove et al. |
| 5,376,112 A | | 12/1994 | Duran |
| 5,522,884 A | * | 6/1996 | Wright ........................ 606/148 |
| 5,584,879 A | * | 12/1996 | Reimold et al. ............ 623/2.37 |
| 5,593,424 A | | 1/1997 | Northup, III |
| 5,607,471 A | | 3/1997 | Sequin et al. |
| 5,662,675 A | * | 9/1997 | Stockert et al. ............. 606/194 |
| 5,716,397 A | * | 2/1998 | Myers ........................ 623/2.36 |
| 5,824,066 A | * | 10/1998 | Gross ......................... 623/2.36 |
| 6,102,945 A | * | 8/2000 | Campbell ................... 623/2.37 |
| 6,159,240 A | * | 12/2000 | Sparer et al. .............. 623/2.36 |
| 6,174,332 B1 | * | 1/2001 | Loch et al. ................. 623/2.37 |
| 6,183,512 B1 | * | 2/2001 | Howance, Jr. et al. ..... 623/2.36 |
| 6,187,040 B1 | * | 2/2001 | Wright ........................ 623/2.36 |
| 6,217,610 B1 | * | 4/2001 | Carpentier et al. ......... 623/2.37 |

* cited by examiner

*Primary Examiner*—David H. Willse
*Assistant Examiner*—Suzette J. Jackson
(74) *Attorney, Agent, or Firm*—Greenberg Traurig, LLP; Todd S. Sharinn

(57) ABSTRACT

An annuloplasty device shaped and sized for attachment to the inner surface of an annulus, the annuloplasty device comprising: a semi-rigid oblong support member having a first end, a second end, a first surface, and a second surface, the first surface including a securing means for securing the first surface to the inner surface of the heart valve annulus, wherein the annuloplasty device is capable of being bent to conform to the inner surface of the annulus such that the first end does not contact the second end.

10 Claims, 3 Drawing Sheets

ANNULOPLASTY RINGS OF PARTICULAR USE IN SURGERY FOR THE MITRAL VALVE

FIELD OF THE INVENTION

The present invention relates to annuloplasty rings or devices for use in heart surgery, and more particularly to novel annuloplasty rings or devices and methods for their use in minimally invasive heart valve replacement or repair surgery. Most particularly, this invention relates to novel annuloplasty rings or devices for use in mitral valve replacement or repair surgery.

BACKGROUND OF THE INVENTION

Human heart valves, such as mitral and tricuspid valves, are sometimes damaged by disease or aging such that the valves no longer properly function. In such cases, heart valve replacement surgery is often indicated. Heart valve replacements and prostheses have been used for many years and many improvements in both the functionality and ease of implantation have been made thereon over time. As used herein, the term "heart valve replacement" is intended to include any mechanical valve, tissue valve, or other device that may be attached to any annulus of a heart be means of a sewing ring. In general, the heart valve comprises a valve body providing a blood flow passageway and oclude means mounted on the valve body for opening and closing the passageway. The valve body has an external, circumferential outer surface. Its dimensions are slightly smaller than the inner surface of the sewing ring implant. This facilitates the valve's body's mating with the inner surface of the sewing ring implant.

Examples of such heart valve replacement apparatus and methods for implanting such heart valve replacement apparatus have been disclosed in U.S. Pat. Nos. 5,071,431; 4,863,460; 4,743,253; 4,655,773; 4,364,126; 4,204,283; 3,898,999; 3,996,623; 3,859,668; 3,534,411; and 3,143,742. Each and every one of the references cited above is hereby incorporated by reference into this application in their entireties to better describe the state of the art.

In some cardiac valve operations, an annuloplasty ring or valvuloplasty ring is used in the repair of the damaged valve, in order to advantageously avoid, in many cases, heart valve replacement. Examples of such annuloplasty rings or valvuloplasty rings have been disclosed in U.S. Pat. Nos. 5,716,397; 5,607,471; 5,593,424; 5,376,112; 5,306,296; 5,163,954; 5,104,407; 5,064,431; 5,061,277; 4,917,698; 4,489,446; 4,290,151; 4,164,046; 4,042,979; and 3,656,185. Each and every one of the references cited above is hereby incorporated by reference into this application in their entireties to better describe the state of the art.

During conventional heart valve repair, annuloplasty rings, such as the CARPENTIER-EDWARDS CLASSIC® annuloplasty ring, have been used to provide support for the repaired native heart annulus and to remodel the annulus into its proper shape and configuration after valve repair. Like most others, the CARPENTIER-EDWARDS CLASSIC® annuloplasty rings are rigid structures designed to encircle the entire native valve annulus, thus forming a nearly complete circumference at the annular level. The shape of the ring is designed to simulate the shape and configuration of a normal valve. Thus, the abnormally shaped valve, which has undergone repair, can be transformed into a valve with a normal shape and configuration through the incorporation of the annuloplasty device.

Conventional annuloplasty rings are secured to the native annulus by sutures that are placed through the native heart annulus and through the conventional annuloplasty ring. This procedure remodels the valve annulus and prevents post-operative dilation of the annulus, which could lead to breakdown of the repair.

Conventional annuloplasty rings have a number of disadvantages. The most noteworthy technical disadvantage is that the annuloplasty ring must be sutured to the anterior part of the annulus, which is sometimes difficult to accomplish, as a significant portion of the anterior part of the annulus needs to be exposed for the suturing to be completed. This limitation of conventional annuloplasty rings is particularly apparent when minimally invasive surgical approaches are utilized, as exposure to the anterior part of the mitral valve annulus is generally restricted by this approach. Further, rigid, complete annuloplasty rings restrict the normal movement of the annulus of the heart at the point of implantation, limiting normal movement of the valve annulus throughout the cardiac cycle. An additional disadvantage associated with these conventional annuloplasty rings is that normal physiologic movement of the annulus is restricted.

Efforts to address some of the drawbacks associated with the previously discussed annuloplasty rings, have, in some cases, yielded rings which do not completely encircle the circumference of the annulus. One such ring which has been used for such procedures is the COSGROVE-EDWARDS® annuloplasty device. This annuloplasty ring incorporates a flexible piece of material for use only in the posterior part of the annulus for reinforcement. Although some of the drawbacks associated with the CARPENTIER-EDWARDS CLASSIC® style rings are obviated by COSGROVE-EDWARDS® annuloplasty device, these devices still have not proved to be an optimum solution for the cardiac surgeon.

As will be more fully addressed infra, the COSGROVE-EDWARDS® annuloplasty device is different from the instant invention because it: (1) is made entirely of a very flexible material, while the instant invention provides a semi-rigid annuloplasty device to support a repaired annulus in a fixed or semi-fixed position; (2) the present invention contains a support member constructed from a shape memory substance such as NITINOL®, so as to be able to return to its original dimensions after deformation; and (3) does not attach to the anterior mitral valve annulus to permit remodeling in the anterior-to-posterior dimension.

Another such annuloplasty device which has been used for such procedures is the CARPENTIER-EDWARDS PHYSIO® annuloplasty ring. This annuloplasty device is a complete ring which incorporates a flexible piece of material which is attached to the entire annulus of the valve. Although some of the drawbacks associated with the CARPENTIER-EDWARDS CLASSIC® style rings are obviated by CARPENTIER-EDWARDS PHYSIO® annuloplasty ring, this device has failed to offer a solution to all of the aforementioned problems associated with annuloplasty rings currently available.

As will be more fully illustrated infra, the CARPENTIER-EDWARDS PHYSIO® annuloplasty device is different from the instant invention because it: (1) is made entirely of a very flexible material, while the instant invention provides a semi-rigid annuloplasty device to support a repaired annulus in a fixed or semi-fixed position; (2) the present invention contains a support member constructed from a shape memory substance such as NITINOL®, so as to be able to return to its original dimensions after deformation; and (3) requires attachment to the complete mitral valve annulus which is unnecessary and sub-optimal for minimally invasive approaches for heart valve surgery.

The instant invention provides a semi-rigid ring designed to attach to the anterior annulus as a key fixation point, providing anterior-posterior remodeling by its design. The semi-rigidity of the instant device, its shape, and the anterior annular fixation points are all necessary for simultaneously achieving good annular remodeling, physiologic movement of the valve annulus, and ease of implantation. Thus, the instant invention provides an apparatus that achieves all of the benefits of the conventional, complete annuloplasty ring, without unnecessary restriction of the valve annulus, and without the need for placing sutures along the entire circumference of the anterior annulus. A device according to the instant invention also achieves better annular remodeling than the COSGROVE-EDWARDS® annuloplasty device by providing significant anterior-to-posterior fixation and narrowing.

SUMMARY OF THE INVENTION

The present invention is directed to annuloplasty rings or devices for use in heart surgery. More particularly, the present invention discloses novel annuloplasty rings, devices and methods for their use in minimally invasive heart valve replacement or repair surgery. As used herein, the terms "annuloplasty ring" or "annuloplasty device" are used interchangeably without regard to whether such device can or does form a closed ring or unbroken annulus. Thus, the annuloplasty device of the instant invention can be referred to as an annuloplasty ring, even though it does not form a closed ring or unbroken annulus.

One aspect of the present invention provides an annuloplasty device shaped and sized for attachment to an inner surface of an annulus. The terms "heart valve annulus" or "native annulus" are intended to designate the anatomical annulus of the heart. The annuloplasty device of this particular aspect, comprises a semi-rigid oblong support member having a first end, a second end, a first surface, and a second surface, the first surface including a securing means for securing the first surface to the inner surface of the heart valve annulus, wherein the annuloplasty device is capable of being bent to conform to the inner surface of the annulus such that the first end does not contact the second end.

In a preferred embodiment of the invention, the semi-rigid oblong support member is manufactured from a shape memory substance such as NITINOL®. Such a material provides the semi-rigid properties of the annuloplasty device necessary to have sufficient flexibility to allow for changes in annular geometry during the cardiac contraction, while ensuring that the device returns to its original shape in an unstressed condition during cardiac relaxation.

In another aspect of the present invention, the annuloplasty device, which is shaped and sized for attachment to the inner surface of an annulus, comprises: a semi-rigid oblong support member covered on at least a portion of its length with a coating to produce a coated support member, the coated support member having a first end, a second end, a first surface, and a second surface, wherein the first surface includes securing means for securing the first surface to the inner surface of the heart valve annulus, and wherein the annuloplasty device is capable of being bent to conform to the inner surface of the annulus such that the first end does not contact the second end.

In a preferred embodiment of the invention, the annuloplasty device is shaped and sized for attachment to a inner surface of a heart valve annulus and is capable of being bent to conform to the inner surface of the heart valve annulus such that the first end does not contact the second end.

In still another preferred embodiment of the invention, the securing means comprises a plurality of apertures adjacent to the first surface of the annuloplasty device for allowing the passage of a securing means to secure the annuloplasty device to the inner surface of the annulus; the plurality of apertures may be distributed uniformly along the first surface. The securing means include sutures, adhesives, staples, and mechanical fasteners.

In yet another preferred embodiment of the invention, the annuloplasty device is made from bio-compatible materials.

In a further preferred embodiment of the invention, the semi-rigid oblong support member bends more readily in one direction than in another direction.

The instant invention also contemplates a kit comprising the annuloplasty device according to the invention, a holder to facilitate placing sutures through the annuloplasty device, and a set of template sizers to enable the surgeon to match the size of the native heart valve annulus and then to choose the appropriate size of the annuloplasty device.

Although the novel annuloplasty rings, devices and methods disclosed herein will be particularly useful in mitral valve replacement or repair surgery, it will become apparent to one of ordinary skill in the art, that the present invention will be useful in a myriad of applications, including but not limited to remodeling of the tricuspid valve.

DETAILED DESCRIPTION OF THE INVENTION

Figure 1:
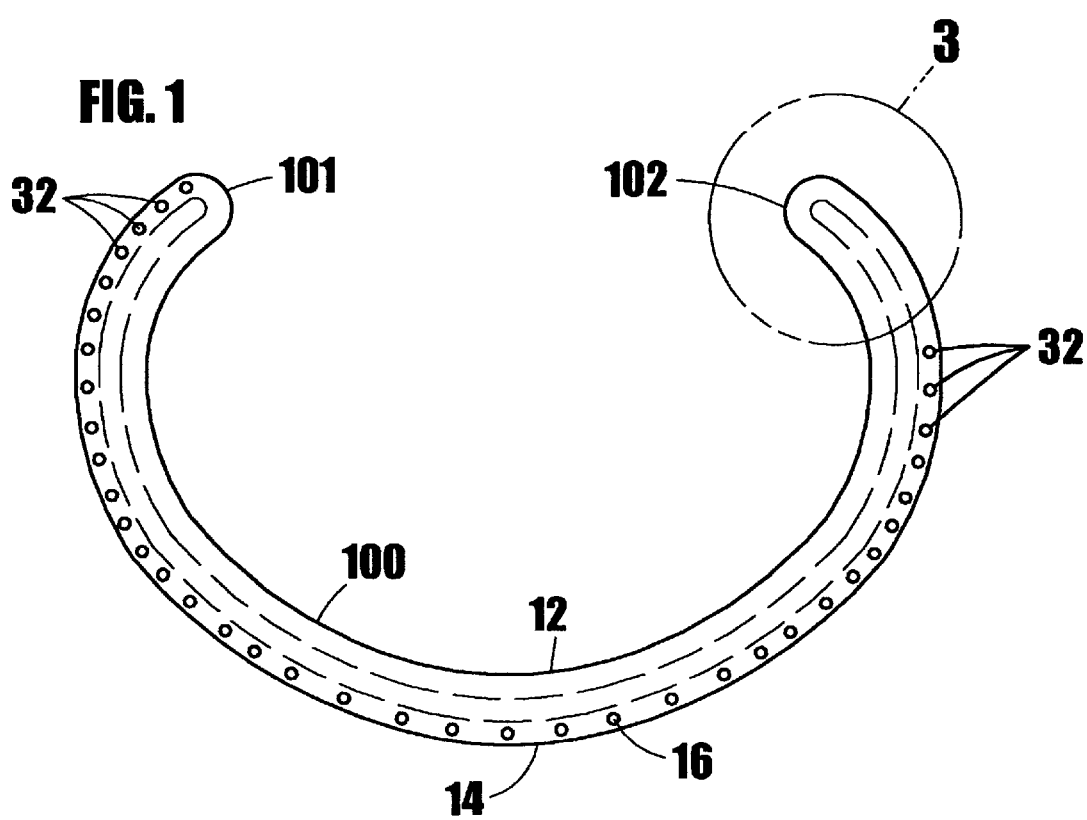
FIG. 1 is a plan view of one embodiment of the annuloplasty ring of the instant invention showing the general shape of the ring.

The instant invention provides a semi-rigid annuloplasty device which is installed in the form of a partial circle. When installed, the annuloplasty device, preferably, does not encircle the entire periphery of the native valve annulus. Rather, it is fixed to two key locations on the lateral and medial edges of the anterior annulus, and also fixed throughout the entire posterior annulus. The present annuloplasty device provides annular remodeling similar to that achieved when using a complete annuloplasty ring. Although the present annuloplasty device may be and in certain embodiments of the invention described herein is, secured to the native valve annulus typically using sutures, may also be secured to the native valve annulus using any other securing means. Such securing means include adhesives, staples, and other mechanical fasteners, and other means known to those of skill in the art.

Since the instant invention does not require placement of sutures or other securing means throughout the entire anterior annulus, its design properties allow the implanting surgeon to accomplish annular remodeling without the need for extensive exposure of the anterior mitral annulus. In heart valve surgery, the annuloplasty device is, however, typically secured to the lateral and medial edges of anterior annulus, just above each valve commissure. While specifically designed for the mitral valve annuloplasty, the instant invention can also be used to provide annuloplasty support of the tricuspid valve.

When implanted, the annuloplasty device is shaped similar to a broad "U". In other words, the two ends do not contact each other. This obviates the need for securing means in the anterior part of the mitral annulus provides the added advantage of avoiding suture placement in the annular areas, which are adjacent to the atrioventricular conduction bundle and the aortic valve in heart surgery.

In fact, the semi-rigid design of this annuloplasty device permits some flexibility to the posterior annulus while providing the requisite support of the valve. Preferably, the flexibility of the device will be of a degree to allow the annuloplasty device to be bent slightly during the cardiac cycle. As the annulus shape changes during the contraction of the heart, the core of the ring specifically exhibits flexibility and memory, which allows it to accommodate the annular changes, while returning to its native shape at the end of the cardiac contraction. Thus, this annuloplasty device permits the surgeon to remodel the valve in both the lateral and anterior-posterior dimensions.

The annuloplasty device will be manufactured in various sizes suited to accommodate the natural range of sizes of the mitral annulus. At the time of surgical implantation, the surgeon, with the aid of a template sizer, will choose the appropriately sized annuloplasty device, and fit the device to the valve annulus.

The instant annuloplasty ring will allow for ease of implantation through limited or minimally invasive approaches, since extensive suturing or other means of securing and exposure of the entire anterior annulus of the heart valve will be rendered unnecessary.

The recent annuloplasty device is particularly suitable for the new minimally invasive procedures that are being utilized in the vast majority major medical centers throughout the United States since it is not sutured or secured to the entire anterior annulus. These procedures require the surgeon to perform all of the implant work through small incisions, where it is often difficult for a surgeon's fingers and hands to reach all areas of the heart or requisite tissue. As noted above and discussed in greater detail below, in heart valve surgery, the instant annuloplasty device will, in most cases, be sutured or secured only from commissure to commissure or slightly above the commissures at the anterolateral and posteromedial commissures of the mitral annulus.

The invention is further described with reference to the figures, which illustrate particular embodiments of the instant invention.

A preferred embodiment of the instant invention is depicted in FIG. 1. As illustrated, Annuloplasty device 100 is shaped and sized for attachment to the inner surface of a heart valve annulus. More precisely, the present invention is shaped to compliment the valve annulus since it is matches the general ovoid shape of the native heart annulus. In this embodiment, the general ratio of the height to the width of the dimensions of the annuloplasty ring are approximately 1.6 to 1. Annuloplasty device 100 includes a semi-rigid oblong support member 16. Support member 16 may be enclosed within annuloplasty device 100, may also be exposed at specific portions of part or over the entire devices length. In certain circumstances support member 16 may form the entire annuloplasty device 100.

Preferably, support member 16 is formed from a shape memory substance, which may include certain metals, alloys and/or plastics. Further, support member 16 may also be designed to bend preferentially or exclusively in one or more directions. Thus, facilitating the bending of the support member 16 to the desired shape, and ensuring that such manipulation of support member 16 will be a more predictable and easier task to accomplish.

For purposes of illustration, annuloplasty device 100 may be divided and discussed in terms of certain sections—namely, first end 101, second end 102, inner surface 12, and outer surface 14. The bottom surface of the device 19 is in contact with the native annulus, while the top surface of the annuloplasty device 20 faces the interior of the atrial chamber of the heart.

First surface 12 includes securing means (not shown) for securing first surface 12 to the inner surface of the heart annulus (not shown). Once secured, the present invention may be bent, as desired by the surgeon, to accommodate the annular motion during the cardiac cycle. Further, as discussed above, annuloplasty device 100 conforms to the inner surface of the heart annulus such that first end 101 preferentially does not contact second end 102.

Figure 2:
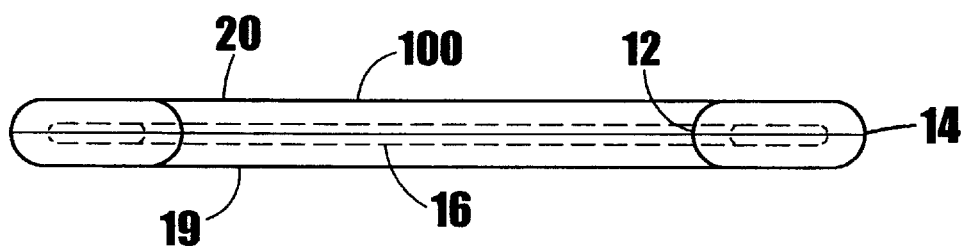
FIG. 2 is a side view of one embodiment of the annuloplasty ring of the instant invention.

As illustrated by FIG. 2 support member 16 is disposed within the present preferred embodiment of annuloplasty device 100. In this embodiment, the support member is fully enclosed within annuloplasty device 100. This orientation will be most beneficial in connection with a cloth covering of the support member; the fabric of covering would allow for penetration of the cloth by sutures to allow for fixation to the native heart tissue. Alternatively, the cloth fabric covering the support member may contain devices to allow to permit autofixation of the annuloplasty ring to the native tissue (not shown).

Figure 3:
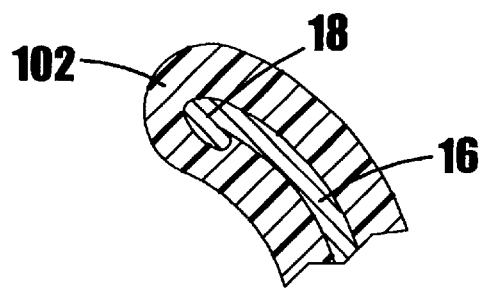
FIG. 3 is a magnified view of the portion of the present invention defined by phantom line 3, showing the structure of one end of the annuloplasty ring.

As highlighted by FIG. 3, the ends of the annuloplasty device 100 (second end 102 as depicted) encasing the ring tip 18 of support member (16) is shaped, as illustrated, to facilitate fixation, and to blunt the tip of the support member to minimize the potential of penetrating the cloth covering.

Figure 4:
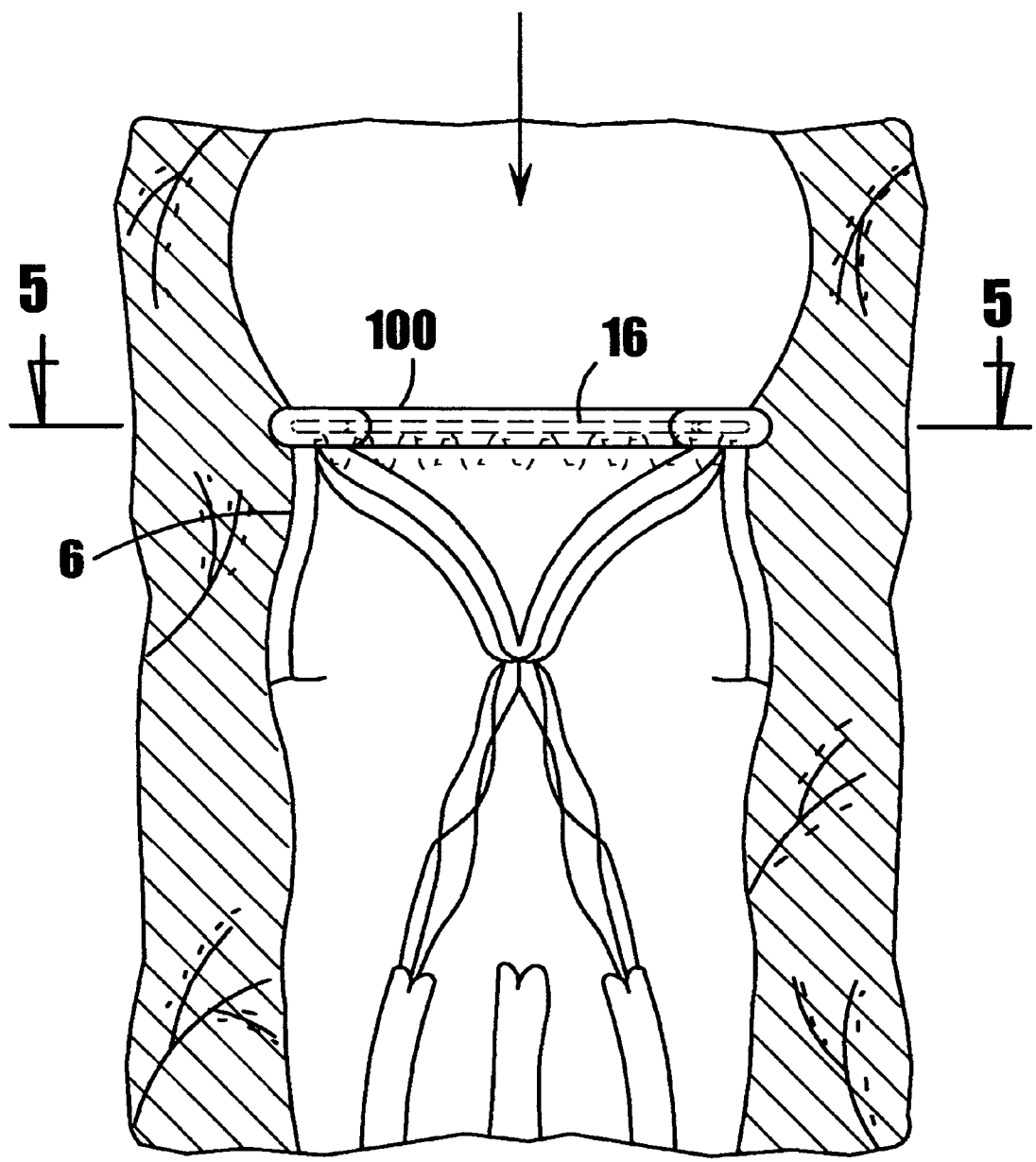
FIG. 4 is a plan view of an embodiment of the annuloplasty ring of the instant invention attached to the native annulus of a heart proximate to the valve thereof
Figure 5:
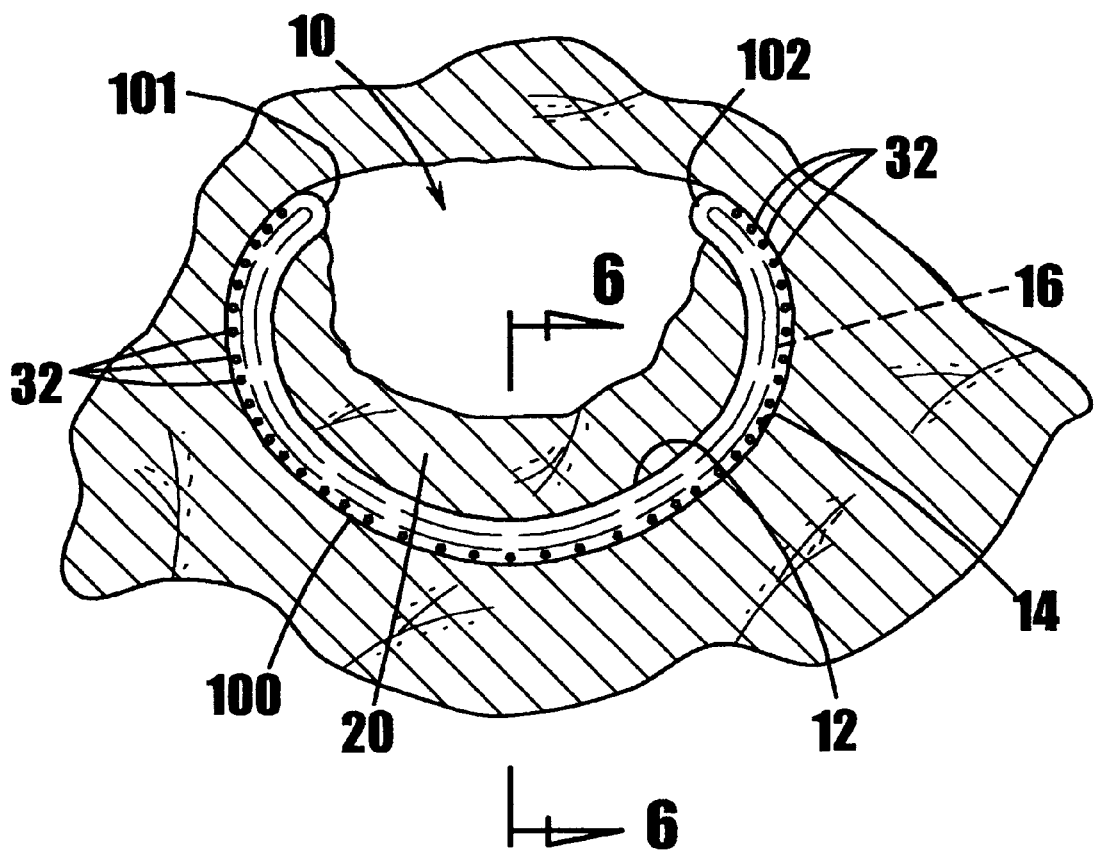
FIG. 5 is a cross-sectional view of one embodiment of the annuloplasty ring of the instant invention attached to a native annulus taken at 5—5.

As FIG. 4 demonstrates, the present annuloplasty ring is generally attached to the native annulus of a heart, proximate to the valve thereof. This is further illustrated through FIG. 5, which also depicts the instant invention attached to the native annulus of a heart, while highlighting the device's orientation therein. Annuloplasty device 100 has multiple openings or apertures 32. Apertures 32 may form a single row along the circumference of the annuloplasty device 100, multiple rows, or may be orientated in a staggered array. The apertures may be evenly or unevenly spaced from each other. These apertures may additionally incorporate corresponding indicia to indicate their location to the surgeon. This indicia can be selected from any variety of visual features or a combination thereof, although the indicia is preferably a distinctive color.

As can be appreciated from FIG. 4, the semi-rigid annuloplasty device 100 will allow some flexibility to the posterior annulus and will allow for the appropriate support of a repaired heart valve, especially one where there has been extensive repair of posterior leaflet 20. Annuloplasty device 100 will also provide the surgeon with an excellent means for remodeling the annulus of the native heart valve particularly where there has been dilatation or stretching.

Figure 6:
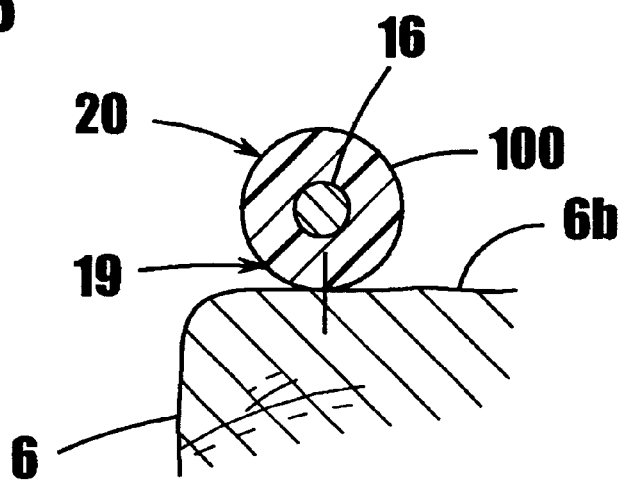
FIG. 6 is a magnified cross-sectional view of an embodiment of the annuloplasty ring of the instant invention, showing the structure of the annuloplasty ring in contact with the native annulus taken at 6—6.

FIG. 6 depicts a cross-sectional view of one embodiment of the instant annuloplasty ring in which the structure of the annuloplasty ring is in contact with the native annulus. In this figure, annuloplasty device 100 is attached to the native heart annulus 6 such that the bottom surface 19 of annuloplasty device 100 contacts the inner surface 6b of native heart annulus 6.

The cross-section (i.e., defined by the plane perpendicular to the semi-rigid oblong support member 16) of the annuloplasty device 100 may be of any generally round shape to provide an appropriate first surface 12 for contact with the inner surface of the heart annulus; such shape may be, without limitation, circular, semicircular, triangular, rectangular, elliptical, round, or ovoid. In this preferred embodiment the ratio of the width to the height of this ovoid shape is preferably 1.6 to 1. As noted above, alternative methods of attaching the annuloplasty device 100 to the native heart annulus 6 may be employed. Such methods include placing sutures completely through the valve annulus and through the annuloplasty device 100. Alternately, autofixation devices and techniques may also be used with the present annuloplasty device.

Turning back to FIG. 5, Annuloplasty device 10 is secured from just above each commissure or the separation between anterior leaflet 10 and posterior leaflet 20 of the heart valve. Preferably, and as depicted, the ends 101 and 102 of the present annuloplasty device do not contact one another once implanted.

As is known in the art, all exposed parts of the annuloplasty ring, including the sutures, should be made of biocompatible materials, either synthetic or natural, from which surgical implants are typically made, for example, polymers, plastics, biological tissue, metals and alloys, and combinations thereof.

As noted above, the figures and examples provided are intended to further describe the aspects of the present invention. Thus, the figures and examples are illustrative only and are not to be construed as limiting the scope of that which is regarded as the invention. Furthermore, while only a single embodiment of the invention has been presented in detail in this disclosure, it will be apparent to those of skill in the art that many modifications, adaptations, and changes may be made thereto without departing from the spirit and scope of the invention. In short, the scope of the present invention is only to be limited by the following claims and the equivalents thereto.

Having thus described the invention, what is claimed is:

1. An annuloplasty device shaped and sized for attachment to an inner surface of an annulus, the annuloplasty device comprising:
    (a) a semi-rigid oblong support member, the support member formed from a temperature responsive shape memory substance, and having a first end, a second end, a first surface, and a second surface;
    (b) the first surface including a securing means for securing the first surface to the inner surface of the heart valve annulus;
    (c) wherein the annuloplasty device is capable of being bent to conform to the inner surface of the annulus such that the first end does not contact the second end; and
    (d) wherein the semi-rigid oblong support member bends more readily in one direction than in another direction.

2. Then annuloplasty device according to claim 1, wherein the support member is covered on at least a portion of its length with a coating to produce a coated support member.

3. The annuloplasty device according to claim 1, wherein the annuloplasty device is shaped and sized for attachment to an inner surface of a heart valve annulus and is capable of being bent to conform to the inner surface of the heart valve annulus such that the first end does not contact the second end.

4. The annuloplasty device according to claim 1, wherein the shape memory substance is an alloy.

5. The annuloplasty device according to claim 1, wherein the shape memory substance is a plastic.

6. The annuloplasty device according to claim 1, wherein the shape memory substance is a metal.

7. The annuloplasty device according to claim 1, wherein the securing means comprises a plurality of apertures adjacent to the first surface of the annuloplasty device for allowing the passage of sutures to secure the annuloplasty device to the inner surface of the annulus.

8. The annuloplasty device according to claim 7, wherein the plurality of apertures are distributed uniformly along the first surface.

9. The annuloplasty device according to claim 1, wherein the securing means is selected from the group consisting of adhesives, staples, and mechanical fasteners.

10. The annuloplasty device according to claim 1, wherein the annuloplasty device is made from biocompatible materials.

* * * * *